(12) United States Patent
Guan et al.

(10) Patent No.: US 7,364,675 B2
(45) Date of Patent: Apr. 29, 2008

(54) SELF-FOLDING POLYMER MICROPARTICLES

(75) Inventors: Jingjiao Guan, Columbus, OH (US); Derek J. Hansford, Columbus, OH (US); L. James Lee, Columbus, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 832 days.

(21) Appl. No.: 10/700,715

(22) Filed: Nov. 4, 2003

(65) Prior Publication Data

US 2004/0191321 A1    Sep. 30, 2004

Related U.S. Application Data

(60) Provisional application No. 60/424,092, filed on Nov. 5, 2002.

(51) Int. Cl.
*B29C 41/00* (2006.01)
*B29C 39/36* (2006.01)

(52) U.S. Cl. ............... 264/5; 264/299; 424/489

(58) Field of Classification Search ........... 156/236, 156/232; 264/5, 140, 460, 621, 636, 299; 424/489
See application file for complete search history.

(56) References Cited

U.S. PATENT DOCUMENTS

| | | | |
|---|---|---|---|
| 5,512,131 A * | 4/1996 | Kumar et al. | 438/738 |
| 6,027,595 A * | 2/2000 | Suleski | 156/230 |
| 6,107,102 A | 8/2000 | Ferrari | |
| 6,158,843 A * | 12/2000 | Murthy et al. | 347/47 |
| 6,180,239 B1 | 1/2001 | Whitesides et al. | |
| 6,221,579 B1 | 4/2001 | Everhart et al. | |
| 6,355,198 B1 | 3/2002 | Kim et al. | |
| 6,518,168 B1 | 2/2003 | Clem et al. | |
| 6,866,801 B1 * | 3/2005 | Mau et al. | 264/29.1 |
| 6,946,322 B2 * | 9/2005 | Brewer | 438/109 |
| 2002/0071869 A1 * | 6/2002 | Bures et al. | 424/487 |
| 2002/0128179 A1 | 9/2002 | Tacon et al. | |
| 2003/0129654 A1 | 7/2003 | Ravkin et al. | |
| 2003/0165778 A1 * | 9/2003 | Makino et al. | 430/302 |
| 2005/0196535 A1 * | 9/2005 | Weigel et al. | 427/271 |

OTHER PUBLICATIONS

"Fabrication of Micrometer-Scale, Patterned Polyhedra by Self-Assembly" by Gracias, et al., *Advanced Materials*, vol. 14, No. 3, Feb. 5, 2002, pp. 235-238.
"Soft Lithography" by Xia, et al., *Annual Reviews Material Science*, vol. 28, 1998, pp. 153-184.

* cited by examiner

*Primary Examiner*—Jill L. Heitbrink
(74) *Attorney, Agent, or Firm*—Calfee Halter & Griswold LLP (57) ABSTRACT

A method for forming three-dimensional polymeric particulate microstructures through self-folding of thin-film microparticles. Self-folding of two-dimensional polymeric precursors produces various three-dimensional particulate microstructures. Dumpling-like microstructures with oil cores and polymer coats are prepared by an interfacial-tension driven self-folding method. Roll-like and bowl-shaped hydrogel microstructures are fabricated by self-folding induced by differential volume shrinkage. Curled microstructures are produced by self-folding that is the result of a two-polymer or bilayer method wherein one of the polymers is a volume changeable polymer.

23 Claims, 5 Drawing Sheets

SELF-FOLDING POLYMER MICROPARTICLES

CROSS-REFERENCE TO RELATED APPLICATIONS

This patent application claims the benefit of U.S. Provisional Patent Application Ser. No. 60/424,092 filed on Nov. 5, 2002 and entitled "Microfabrication of Polymer Microparticles," the disclosure of which is incorporated as if fully rewritten herein.

STATEMENT REGARDING FEDERALLY FUNDED RESEARCH

This invention was made with government support under award number DMI-0084919 awarded by The National Science Foundation. The Government has certain rights in the invention.

TECHNICAL FIELD OF THE INVENTION

The present invention relates generally to methods for fabricating microparticles for use in scientific and/or medical applications and more specifically to a method for creating polymer microparticles having certain three-dimensional characteristics.

BACKGROUND OF THE INVENTION

Microparticulate systems that utilize one or more polymers are widely used for biomedical applications such as drug delivery, bio-analysis, and clinical diagnosis. However, the particles produced by conventional manufacturing methods are typically limited to a spherical shape, relatively wide size distributions, and symmetrical monolithic or core-shell structures. While spherical microparticles are useful for certain applications such as drug delivery, non-spherical particles may have more desirable characteristics. For example, discrete control of particle geometry may facilitate more precise bio-analysis and controlled drug delivery because the shape of a particle can be tailored to function more effectively under certain predefined conditions. Thus, there is a need for a method for fabricating microparticles in a variety of three-dimensional shapes and geometric configurations.

Microfabrication techniques conventionally used for making integrated circuits have been utilized to create microparticles by combining silicon dioxide or polymethylmethacrylate (PMMA) and a photo-sensitive polymer. These techniques can be used to create microparticles having a precise shape, uniform size and specifically designed structures and surface chemistries, thereby making them suitable for use as drug-carrying vehicles. However, these techniques are limited in that they (i) require the use of photolithography to create every particle and (ii) are compatible with only certain materials. Moreover, the rigorous conditions, including highly aggressive solutions and elevated temperatures, which are used to release fabricated microparticles into solution may damage fragile compounds that have been incorporated into the microparticles. Thus, there are significant limitations to using known photolithographic techniques for microfabrication of microparticles.

An alternative to conventional photolithographic techniques is soft-lithography. Soft lithography is a collective term that refers to a group of non-photolithographic microfabrication techniques that employ elastomeric stamps having certain three dimensional relief features to generate micro-structures and even nano-structures. A more detailed description of soft lithography is found in Xia and Whitesides, *Annual Review of Materials Science* 28: 153-84 (1998) incorporated herein by reference. Thus, there is a need to utilize alternate microfabrication techniques such as soft lithography to create polymer microparticles having certain desired geometries.

SUMMARY OF THE INVENTION

These and other deficiencies of the prior art are overcome by the present invention, the exemplary embodiment of which provides a method for forming three-dimensional polymeric particulate microstructures through self-folding of thin-film microparticles. According to the methods of the present invention, self-folding of two-dimensional polymeric precursors produces various three-dimensional particulate microstructures. Dumpling-like microstructures with oil cores and polymer coats are prepared by an interfacial-tension driven self-folding method. Roll-like and bowl-shaped hydrogel microstructures are fabricated by self-folding, induced by differential volume shrinkage. Curled microstructures are produced by self-folding that is the result of a two-polymer or bilayer method. These techniques provide a relatively simple method for fabricating three-dimensional polymeric microstructures that are often difficult to produce by other methods, and may lead to low-cost fabrication of particulate-like microdevices with three-dimensional structures for applications such as advanced drug delivery and cell encapsulation.

Further advantages of the present invention will become apparent to those of ordinary skill in the art upon reading and understanding the following detailed description of the preferred embodiments.

BRIEF DESCRIPTION OF THE DRAWINGS

The accompanying drawings, which are incorporated into and form a part of the specification, schematically illustrate one or more exemplary embodiments of the invention and, together with the general description given above and detailed description of the preferred embodiments given below, serve to explain the principles of the invention.

FIG. 4b is an optical micrograph of three-dimensional structures made from foldable PMAA/PHEMA bilayer strips according to the method of FIG. 4a.

DETAILED DESCRIPTION OF THE INVENTION

Interfacial Tension Driven Method

Figure 1A:
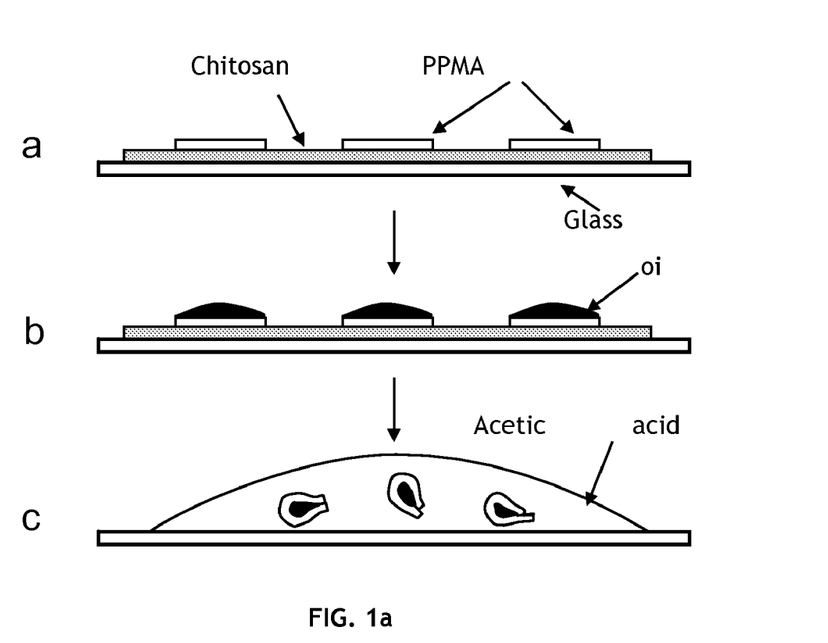
FIG. 1a is a schematic illustration of the embodiment of the present invention that utilizes an interfacial tension driven method for fabricating dumpling-like oil-in-PPMA three-dimensional microstructures.
Figure 1B:
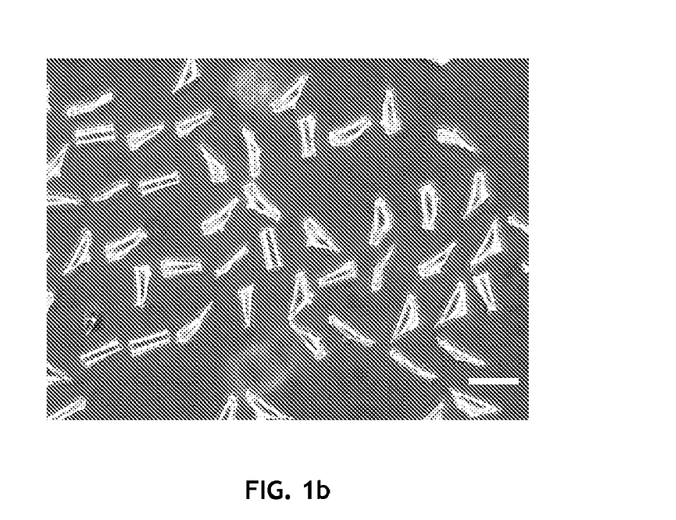
FIG. 1b is an optical micrograph of the dumpling-like oil-in-PPMA microstructures fabricated by the method of FIG. 1a in aqueous solution of acetic acid (scale bar=50 µm).

A first embodiment of the method of the present invention is referred to as the "interfacial tension driven method." With reference to FIGS. 1a-b, this method involves the following steps for creating self-folding polymer microparticles:

First, polymeric micropads are printed on a substrate that has been coated with a dissolvable "sacrificial" layer of material. In the exemplary embodiment of FIG. 1a, 40 μm-wide square poly (propyl methacrylate) (PPMA) micropads are printed on a chitosan-coated glass slide by a technique known as microContact Hot Printing ("μCHP") which utilizes a poly (dimethyl siloxane) (PDMS) stamp. This technique is disclosed in U.S. patent application Ser. No. 10/656,661 filed on Sep. 5, 2003, entitled "Microfabrication of Polymer Microparticles," the entire specification of which is hereby incorporated by reference.

Second, a thin layer of oil is applied to the substrate such that the oil only accumulates on the micropads. In an exemplary embodiment, food-grade soybean oil is applied to the slide, leaving oil droplets only on the PPMA micropads due, presumably, to the polarity differences between oil, PPMA and chitosan.

Third, a solvent is added to dissolve the sacrificial layer and release the printed micropads into solution. In the exemplary embodiment of FIG. 1a, aqueous acetic acid solution is added to release the micropads by dissolving the chitosan sacrificial layer. The released micropads fold over the oil droplets spontaneously, forming the dumpling-like microstructures shown in the optical micrograph of FIG. 1b. FIG. 1b is an optical micrograph of the dumpling-like oil-in-PPMA microstructures in aqueous solution of acetic acid (scale bar=50 μm).

Presumably, the selective wetting of the micropads by the oil is a result of minimization of interfacial energy of the system due to low surface tensions of PPMA and oil and the high surface tension of chitosan. The folding of the micropads is most-likely driven by free-energy minimization as water replaces air in the system. Since the oil-water interfacial tension is larger than that of oil-air and PPMA-water, the oil droplets that initially spread on the micropads tend to shrink into a spherical shape to minimize their interfacial area in contact with water. Also, due to the strong adhesion between oil and PPMA, and the response of the micropads, the oil droplets force the released micropads to fold around them. The final structures are dumpling-like microcapsules with oil cores and PPMA outer coats.

Thus, the self-folding polymer system of this first embodiment includes an oil as a shrinking liquid with low surface tension, micropads formed from PPMA having low surface tension that allows the oil wet the micropads, chitosan as a dissolvable layer with high surface tension that prevents the oil from wetting the sacrificial layer and allows the oil to accumulate on micropads, and water as a solvent with high surface tension that dissolves the chitosan and induces the shrinkage of the oil droplets. Generally speaking, the oil/PPMA/chitosan/water system is a LST (low surface tension)/LST/HST (high surface tension)/HST system. Other materials can be used with this method if they have these general characteristics. In principle, this HST/HST/LST/LST system is ideally suited for fabrication of dumpling-like microstructures due to the use of an aqueous solution as a shrinking liquid, a hydrophilic polymer for the micropads, a hydrophobic dissolvable layer, and a hydrophobic solvent to release the micropads and induce self-folding of the microparticles.

Property Gradient Method

Figure 2A:
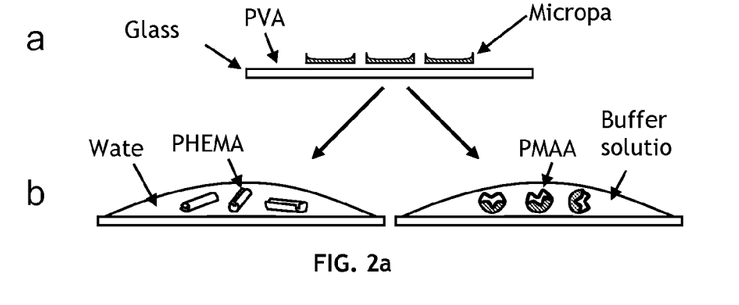
FIG. 2a is a schematic illustration of the embodiment of the present invention that utilizes a property gradient method for fabricating PHEMA and PMAA 3-D microstructures.
Figure 2B:
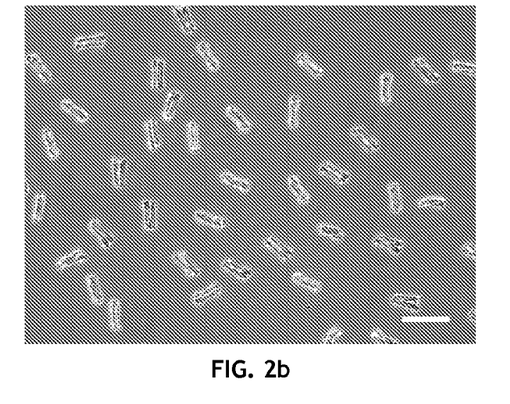
FIG. 2b is an optical micrograph of the roll-like PHEMA microstructures fabricated by the method of FIG. 2a in water and formed from 40 µm-wide square micropads (scale bar=50 µm).
Figure 2C:
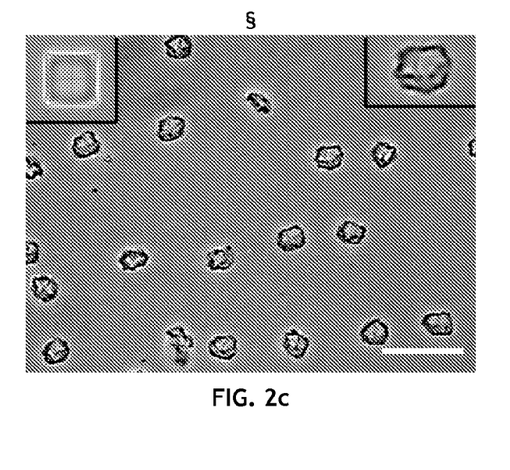
FIG. 2c is an optical micrograph of the bowl-shaped PMAA microstructures fabricated by the method of FIG. 2a in buffer solution with pH of 10 and formed from 30 µm-wide square micropads. The upper left insert of FIG. 2c shows a 30 µm-wide square micropad before released into solution. The upper right insert of FIG. 2c shows a twice-magnified bowl-shaped PMAA microstructure (scale bar=100 µm).

A second embodiment of the method of the present invention is referred to as the "property gradient method." This embodiment induces self-folding of hydrogel micropads to form three dimensional microstructures. With reference to FIGS. 2a-c, this method involves the following steps for creating self-folding polymer microparticles:

First, polymeric (i.e, hydrogel) micropads are printed on a substrate coated with a dissolvable or "sacrificial" layer using a PDMS stamp as described above. In the exemplary embodiment of FIGS. 2a-c, poly (hydroxyethyl methacrylate) (PHEMA) and poly (methacrylic acid) (PMAA) are used as the hydrogel component; however, other volume-changeable hydrogels are also compatible with this method. The PDMS stamp used for preparing PHEMA microstructures includes 40 μm-wide and 1.4 μm-deep square microwells separated by 10 μm-wide ridges. The PDMS stamp used for preparing the PMAA microstructures includes 30 μm-wide and 1.1 μm-deep square microwells separated by 20 μm-wide ridges.

Monomer hydrogel precursor solutions are typically cured (partially) before transfer to the wells of the PDMS stamp. Pre-curing increases the viscosity of the pre-polymer layers, thereby making them less likely to rupture in the wells. Partially curing the monomer solutions also lowers the evaporation rate of volatile liquids such as the MAA monomer in the shallow wells of the stamp.

In the exemplary embodiment of FIGS. 2a-c, the HEMA monomer (98.6 wt %) with Irgacure 651 (2,2-dimethoxy-2-phenylacetophenone, 1.4 wt %) as photoinitiator in a closed bottle was exposed to UV for 4 minutes until a viscous medium was obtained. The crosslinking agent TEGDMA (triethylene glycol dimethacrylate) with a molar ratio of 2.4:100 to the initial HEMA monomer was then added. Likewise, the MAA monomer (53.2 wt %), solvent DMSO (46.1 wt %), and photoinitiator Irgacure 651 (0.7 wt %) was exposed to UV for 8 minutes in a closed bottle. The crosslinking agent TEGDMA with a molar ratio of 5.2:100 to the initial MAA monomer was then added.

The mixed viscous solutions were placed in the microwells by discontinuous wetting and further exposed to UV for 20 minutes under blowing nitrogen. The fully cured polymer in the microwells was then printed as micropads onto a poly(vinyl alcohol) (PVA)-coated glass slide.

Second, a solvent is added to dissolve the sacrificial layer and release the micropads into solution. The released micropads fold spontaneously or fold in the presence of a certain stimulus such as a change in pH. In the exemplary embodiment of FIGS. 2a-c, water and a buffer solution with a pH of 4.0 was added to dissolve the polyvinyl alcohol (PVA) sacrificial layer.

As shown in the optical micrographs of FIGS. 2b and 2c, the released micropads spontaneously fold into roll-like structures (see FIG. 2b) or bowl-shaped structures (see FIG. 2c). FIG. 2b is an optical micrograph of the roll-like PHEMA microstructures in water and formed from 40 μm-wide square micropads (scale bar=50 μm). FIG. 2c is an optical micrograph of the bowl-shaped PMAA microstructures in buffer solution with pH of 10 and formed from 30 μm-wide square micropads. The upper left insert of FIG. 2c shows a 30 μm-wide square micropad before released into solution. The upper right insert of FIG. 2c shows a twice-magnified bowl-shaped PMAA microstructure (scale bar=100 μm).

The spontaneous folding of the microparticles in this embodiment is likely due to a heterogeneous volume change along the thickness direction and/or in the plane of the micropads due to property gradients along the thickness direction and/or in the plane of the micropads. After being printed on the substrate, the top surface of the micropads will have higher "molded-in" stresses. Relaxation of this gradient stress is expected to cause upward-folding of the micropads. However, to form roll-like structures, uniaxial folding of individual micropads is required. Relaxation of anisotropic stress in the dragging direction may be responsible for the uniaxial folding of the micropads. Non-uniform crosslinking density across the plane of micropads may be responsible for the formation of bowl-shaped PMAA microstructures.

Bilayer Method

Figure 3A:
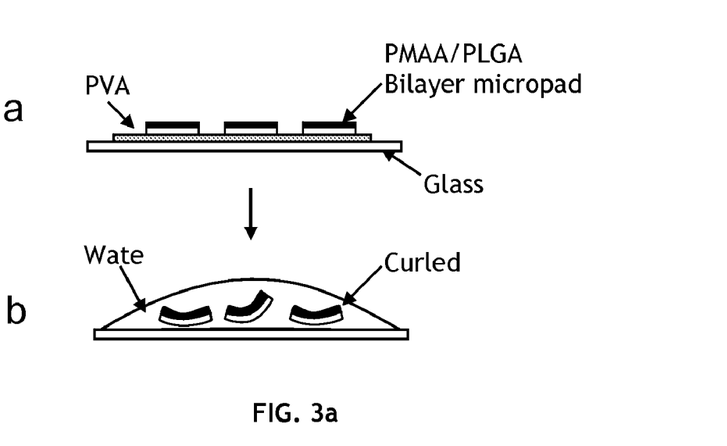
FIG. 3a is a schematic illustration of the embodiment of the present invention that utilizes a bilayer method for fabricating curled PMAA/PLGA bilayer microstructures.
Figure 3B:
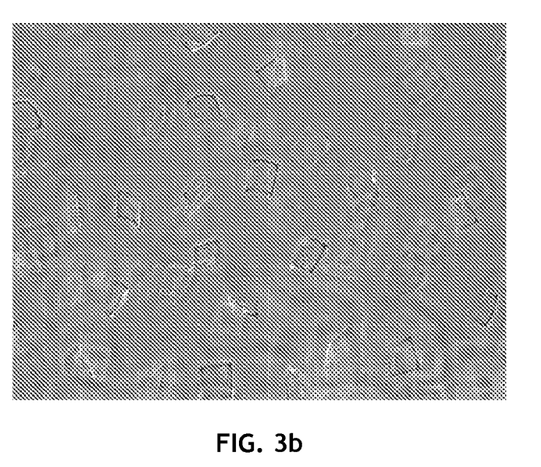
FIG. 3b is an optical micrograph of the curled PMAA/PLGA bilayer microstructures fabricated by the method of FIG. 3a in water (scale bar=100 μm).

A third embodiment of the method of the present invention is referred to as the "bilayer method." With reference to FIGS. 3a-b, this method involves the following steps for creating self-folding polymer microparticles:

First, bilayer polymeric micropads are printed on a substrate coated with a dissolvable or "sacrificial" layer using a PDMS stamp as described in U.S. patent application Ser. No. 10/656,661. Second, a solvent is added to dissolve the sacrificial layer and release the micropads into solution. The released micropads curl spontaneously or curl in the presence of a certain stimulus such as a change in pH. In the exemplary embodiment of FIGS. 3a-b, 40 μm-wide square microparticles were fabricated using a PMAA/PLGA (polylactic-co-glycolic acid) bilayer. FIG. 3b is an optical micrograph of the curled PMAA/PLGA bilayer microstructures in water (scale bar=100 μm).

The spontaneous curling of the microparticles in this embodiment is likely due to a differential volume change of the two polymer layers. The PMAA layer swells in water while PLGA does not have volume or shape change, leading to the slight curling of the micropads. Thus, a variety of other polymers are compatible with this method provided that one of the two layers is volume-changeable and the two layers have different volume-changing ratios.

Figure 4A:
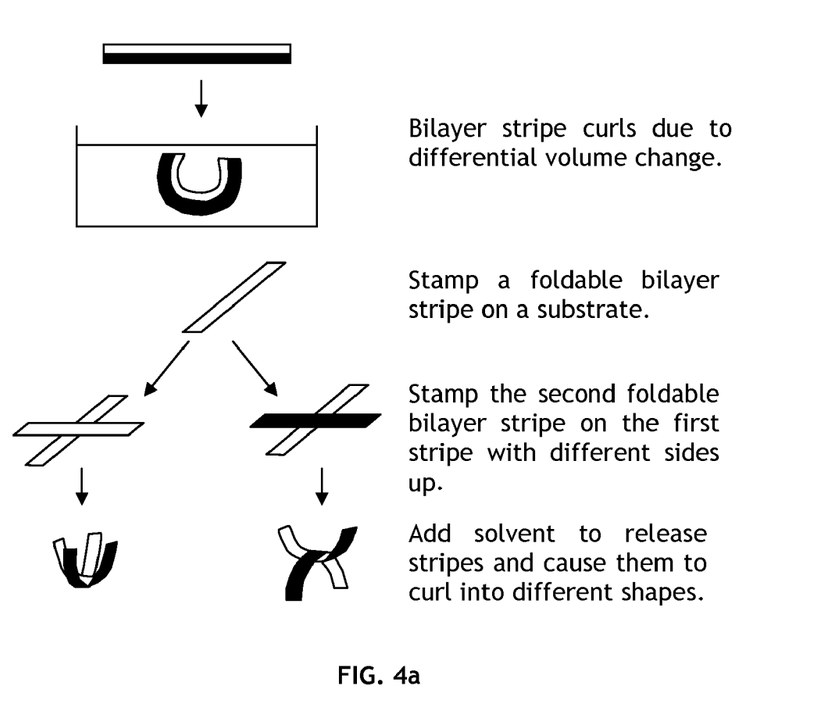
FIG. 4a is a schematic illustration of the embodiment of the present invention that fabricates three-dimensional microstructures by a method that includes double stamping of foldable bilayer strips.
Figure 4B:
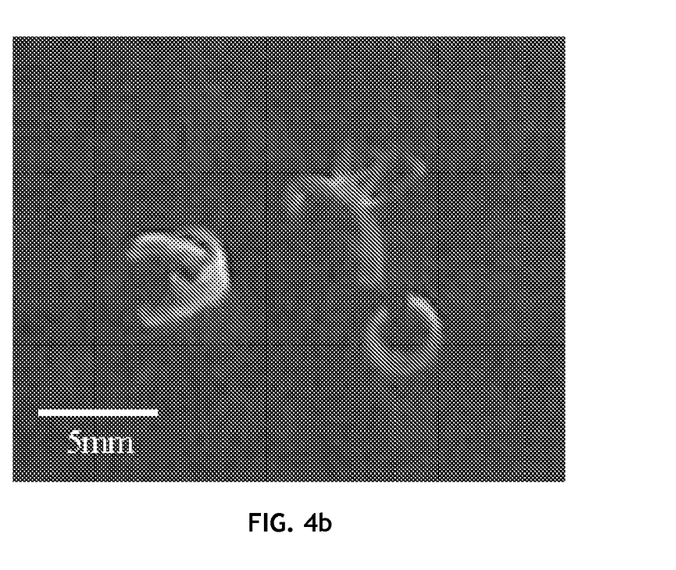

The final three-dimensional geometries of the microstructures fabricated by the methods of the present invention can be further controlled by pre-designing that lateral shapes of the "two dimensional" (i.e., flat) micropads. The three general embodiments of the method described herein, as well as the techniques disclosed in U.S. patent application Ser. No. 10/656,661 can be combined to fabricate microstructures having more versatile structures. For example, using foldable bilayer rectangular micropads and double the stamping technique, microstructures in shown in FIG. 4a can be fabricated. FIG. 4b is an optical micrograph of the macroversion of the three-dimensional structures made from foldable PMAA/PHEMA bilayer strips according to this method.

Figure 5A:
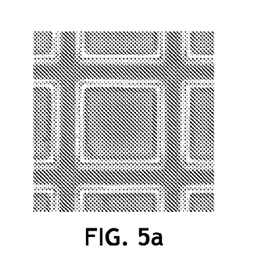
FIG. 5a is an optical micrograph of a 40 μm wide square PMAA micropad on PVA.
Figure 5B:
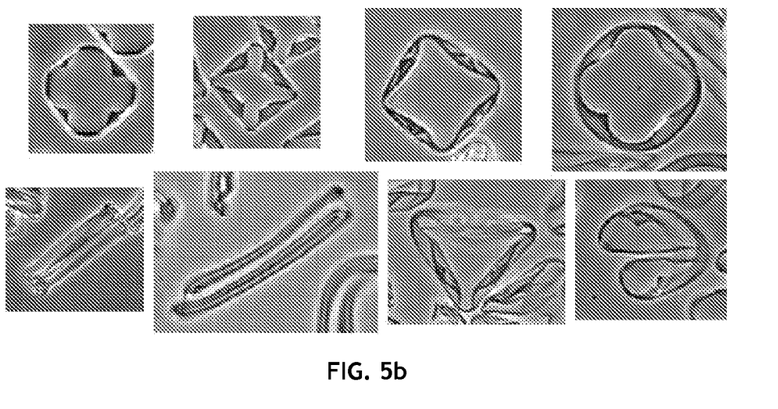
FIG. 5b is a series of optical micrograph of microstructures formed by self-folding of released PMAA micropads in neutral water.
Figure 5C:
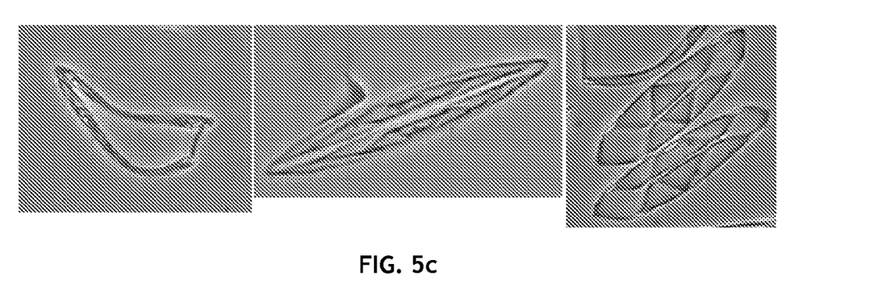
FIG. 5c is a series of optical micrographs of microstructures formed by self-folding of released PMAA micropads in buffer solution having a pH of 10.

Other three-dimensional PMAA microstrucutres formed by self-folding are shown in FIGS. 5a-c. FIG. 5a is an optical micrograph of a 40 μm wide square PMAA micropad on PVA. FIG. 5b is a series of optical micrograph of microstructures formed by self-folding of released PMAA micropads in neutral water. FIG. 5c is a series of optical micrographs of microstructures formed by self-folding of released PMAA micropads in buffer solution having a pH of 10.

PPMA was obtained from Monomer-Polymer & Dajac Laboratory (Feasterville, Pa.). TEGDMA (triethyleneglycol dimethacrylate), Irgacure 651 (2,2-Dimethoxy-2-phenylacetophenone), acetone, HEMA, DMSO and chitosan were obtained from Sigma-Aldrich. PVA (88 mol % hydrolyzed, 25,000 Da) and PDMS (T2) were obtained from Polysciences, Inc. (Warringto, Pa., USA) and Dow-Corning, respectively. Buffer solutions with a pH=4.0 (SB 101-500) and glass slides were purchased from Fisher Scientific. A Nikon TMS inverted optical microscope and a Fujifilm Finepix 2600 digital camera were used to take micrographs. A hot plate was used to heat glass slides and the temperature was measured by a thermocouple. The UV source was a UV/WL table (Vilber Lourmat, Marne-La-Vallée, France) producing 312 nm UV light. UV-curing was carried out in a box under blowing nitrogen.

The polymer microparticles of the present invention are useful for a variety of applications. Microparticles made by the interfacial tension driven method may be used for drug encapsulation. When oil is encapsulated in hydrophobic micropads, oil-soluble drugs can be dissolved in the encapsulated oil droplets, whereas water-soluble drugs can be dispersed in the form of solid powder or emulsion in the encapsulated oil droplets. Using the oil-based system as a model, presumably when an aqueous solution is encapsulated in hydrophilic micropads, water-soluble drugs can be dissolved or dispersed in the form of liposomes in the encapsulated aqueous droplets, whereas oil-soluble drugs can be dispersed in the form of emulsion in the encapsulated aqueous droplets.

All three embodiments of the present invention may be used to encapsulate cells for applications such as carrying and protecting cells in bioreactor and serving as a three-dimensional scaffold for tissue engineering. For the first embodiment, self-folding can be induced by tensile stress generated by the cells growing on micropads. For the second and third embodiments, the tensile stress generated by cells growing on micropads is not necessary because micropads can fold spontaneously and encapsulate cells. Therefore, cells do not have to grow on the micropads.

Three-dimensional microstructures with discretely controlled geometries may be useful for drug delivery by the pulmonary route. Furthermore, the methods disclosed herein may be used to make environment-sensitive polymer-based microdevices having three dimensional structures that change their shape in response to environmental stimuli.

While the above description contains many specificities, these should not be construed as limitations on the scope of the invention, but rather as exemplification of certain preferred embodiments. Numerous other variations of the present invention are possible, and is not intended herein to mention all of the possible equivalent forms or ramifications of this invention. Various changes may be made to the present invention without departing from the scope or spirit of the invention.

What is claimed:

1. A method for fabricating polymer microparticles, comprising the steps of:
   (a) coating a polymer stamp with a polymeric solution to create a continuous layer of polymer on said stamp, wherein said stamp further comprises a plurality of microstructures on at least one side of said stamp for receiving said polymeric solution, and wherein said microstructures further comprise a plurality of micro-pillars and a plurality of micro-wells;
   (b) removing said layer of polymer from said micro-pillars;
   (c) creating polymer microparticles by transferring said layer of polymer from said micro-wells onto a substrate, wherein said substrate further comprises a layer of dissolvable material covering said substrate;
   (d) applying a thin layer of oil to said substrate to selectively cover said microparticles; and
   (e) placing said substrate in a solvent to dissolve said dissolvable material and release said microparticles into solution.

2. The method of claim 1, wherein said stamp is a polydimethyl siloxane stamp.

3. The method of claim 1, wherein said polymeric solution further comprises poly (propyl methacrylate).

4. The method of claim 1, wherein said substrate is a glass slide.

5. The method of claim 1, wherein said layer of dissolvable material further comprises chitosan.

6. The method of claim 1, wherein said oil further comprises food-grade soybean oil.

7. The method of claim 1, wherein said solvent further comprises acetic acid.

8. A method for fabricating polymer microparticles, comprising the steps of:
   (a) coating a polymer stamp with a partially cured liquid hydrogel precursor, wherein said stamp further comprises a plurality of microstructures on at least one side of said stamp for receiving said hydrogel precursor, and wherein said microstructures further comprise a plurality of micro-pillars and a plurality of micro-wells;
   (b) completely curing said partially cured liquid hydrogel precursor to create a substantially solid hydrogel in said micro-wells;
   (c) creating hydrogel microparticles by transferring said cured hydrogel from said micro-wells onto a substrate, wherein said substrate further comprises a layer of dissolvable material covering said substrate; and
   (d) placing said substrate in a solvent to dissolve said dissolvable material and release said microparticles into solution.

9. The method of claim 8, wherein said stamp is a polydimethyl siloxane stamp.

10. The method of claim 8, wherein said hydrogel solution further comprises polyhydroxyethyl methacrylate or polymethacrylic acid.

11. The method of claim 8, wherein said substrate is a glass slide.

12. The method of claim 8, wherein said layer of dissolvable material further comprises polyvinyl alcohol.

13. The method of claim 8, wherein said solvent further comprises water and a buffer solution.

14. The method of claim 8, wherein the cured hydrogel from the micro-wells is transferred onto the substrate in a maimer such that the cured hydrogel directly contacts the layer of dissolvable material on the substrate.

15. The method of claim 8, wherein the microparticles consist essentially of substantially solid hydrogel.

16. A method for fabricating polymer microparticles, comprising the steps of:
   (a) coating a polymer stamp with a partially cured liquid hydrogel precursor, wherein said stamp further comprises a plurality of microstructures on at least one side of said stamp for receiving said hydrogel precursor, and wherein said microstructures further comprise a plurality of micro-pillars and a plurality of micro-wells;
   (b) completely curing said partially cured liquid hydrogel precursor to create a substantially solid hydrogel in said micro-wells;
   (c) coating said stamp with a second polymeric solution to create a continuous layer of polymer on said stamp;
   (d) removing said layer of polymer from said micro-pillars;
   (e) creating bi-layer polymer microparticles by transferring said polymers from said micro-wells onto a substrate, wherein said substrate further comprises a layer of dissolvable material covering said substrate; and
   (f) placing said substrate in a solvent to dissolve said dissolvable material and release said bilayer microparticles into solution.

17. The method of claim 16, wherein said stamp is a polydimethyl siloxane stamp.

18. The method of claim 16, wherein said hydrogel and second polymer solution further comprise polymethacrylic acid and polylactic-co-glycolic acid, respectively.

19. The method of claim 16, wherein said substrate is a glass slide.

20. The method of claim 16, wherein said layer of dissolvable material further comprises polyvinyl alcohol.

21. The method of claim 16, wherein said solvent further comprises water.

22. The method of claim 16, wherein the hi-layer polymer microparticles are created by transferring said polymers from said micro-wells directly onto the dissolvable material on the substrate.

23. The method of claim 16, wherein the microparticles consist essentially of substantially solid hydrogel and the polymer of said second polymer solution.

* * * * *

UNITED STATES PATENT AND TRADEMARK OFFICE
CERTIFICATE OF CORRECTION

PATENT NO. : 7,364,675 B2  
APPLICATION NO. : 10/700715  
DATED : April 29, 2008  
INVENTOR(S) : Jingjiao Guan, Derek J. Hansford and L. James Lee

Page 1 of 1

It is certified that error appears in the above-identified patent and that said Letters Patent is hereby corrected as shown below:

In the Specification

Column 1, Line 17 should read:
This invention was made with government support under grant number DMI0084919 awarded by the National Science Foundation. The government has certain rights in the invention.

Signed and Sealed this
Twenty-first Day of July, 2020

Andrei Iancu
*Director of the United States Patent and Trademark Office*